United States Patent [19]  [11] 4,188,389
Jirkovsky  [45] Feb. 12, 1980

[54] 1,2,3,4-TETRAHYDROPYRROLO(1,2-A)PYRAZINES

[75] Inventor: Ivo L. Jirkovsky, Montreal, Canada

[73] Assignee: Ayerst McKenna & Harrison, Inc., Montreal, Canada

[21] Appl. No.: 957,602

[22] Filed: Nov. 3, 1978

[51] Int. Cl.$^2$ ............... A61K 31/495; C07D 487/04
[52] U.S. Cl. ................................. 424/250; 544/349
[58] Field of Search .................... 544/349; 424/250

[56] References Cited

U.S. PATENT DOCUMENTS

| | | | |
|---|---|---|---|
| 2,655,512 | 10/1953 | Dunlop et al. | 260/326.5 |
| 2,673,850 | 3/1954 | Stoll et al. | 544/349 |
| 3,164,598 | 1/1965 | Freed | 544/349 |
| 4,093,616 | 6/1978 | Kuhla | 544/349 |
| 4,097,598 | 6/1978 | Kuhla | 424/256 |

FOREIGN PATENT DOCUMENTS 237153 11/1969 U.S.S.R. .................................. 544/349

OTHER PUBLICATIONS

Herz et al., "J. Amer. Chem. Soc.", vol. 77 (1955), pp. 6355–6357.
Dunlop et al., "Chem. Abstracts," vol. 48 (1954), Col. 11495f.
Flament et al., "Helvetica Chimica Acta", vol. 60 (1977), pp. 1872–1883.
Morimoto et al., "Chemical Abstracts", vol. 82 (1975), Col. 140180b.
Morimoto et al., "Chemical Abstracts", vol. 82 (1975), Col. 156398q.
Morimoto et al., "Chemical Abstracts", vol. 82 (1975), Col. 125416q.

Primary Examiner—Alton D. Rollins
Assistant Examiner—James H. Turnipseed
Attorney, Agent, or Firm—Arthur E. Wilfond

[57] ABSTRACT

1,2,3,4-tetrahydropyrrolo(1,2-a)pyrazine derivatives characterized by having a lower alkyl, cyclo(lower)alkyl, phenyl or substituted phenyl at position 1 of the nucleus and optionally further substituted at position 2 of the nucleus with a lower alkyl, cyclo(lower)alkyl, phenyl(lower)alkylene or 2-(indole-3-yl)ethyl are disclosed. The derivatives are useful antidepressant agents. Methods for their preparation also are disclosed.

12 Claims, No Drawings

1,2,3,4-TETRAHYDROPYRROLO(1,2-A)PYRAZINES

BACKGROUND OF THE INVENTION (a) Field of the Invention

This invention relates to novel 1,2,3,4-tetrahydropyrrolo(1,2-a)pyrazine derivatives, to therapeutically acceptable acid addition salts thereof, to processes for their preparation and to pharmaceutical compositions of the derivatives.

More specifically, the present invention relates to novel 1,2,3,4-tetrahydropyrrolo(1,2-a)pyrazine derivatives having a substituent at position 1 and optionally further substituted at position 2. These derivatives are useful as antidepressant agents.

(b) Description of the Prior Art

A number of compounds having a pyrrolo(1,2-a)pyrazine nucleus have been reported. For example, 1-methylpyrrolo(1,2-a)pyrazine is described by W. Herz and S. Tocker, J. Amer. Chem. Soc., 77 6355(1955). 1-Methyl-3,4-dihydropyrrolo(1,2-a)pyrazine as well as substituted pyrrolo(1,2-a)pyrazine derivatives are reported by I. Flament et al., Helv. Chim. Acta, 60, 1872(1977), see also A. P. Dunlop and S. Swadesh, U.S. Pat. No. 2,655,512, issued Oct. 13, 1953.

SUMMARY OF THE INVENTION

The compounds of this invention are represented by formula I

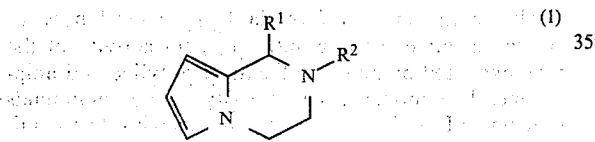

in which $R^1$ is lower alkyl, cyclo(lower)alkyl, phenyl or phenyl mono-, di- or trisubstituted with lower alkyl or lower alkoxy and $R^2$ is hydrogen, lower alkyl, cyclo(lower)alkyl, 2-(indole-3-yl)ethyl or phenyl(lower) alkylene.

A preferred group of compounds are represented by formula I in which $R^1$ is lower alkyl, phenyl or phenyl mono-, di- or trisubstituted with lower alkyl or lower alkoxy and $R^2$ is hydrogen, lower alkyl, 2-(indole-3-yl)ethyl or phenyl(lower)alkylene.

A most preferred group of compounds are represented by formula I in which $R^1$ is lower alkyl, phenyl or 2,3,4-trimethoxyphenyl and $R^2$ is hydrogen, lower alkyl, 2-(indole-3-yl)ethyl or 2-phenylethyl.

The therapeutically acceptable acid addition salts of the compounds of formula I are included within the scope of this invention.

The compounds of formula I or a therapeutically acceptable acid addition salt thereof can be prepared by:

(a) cyclizing a compound of formula II

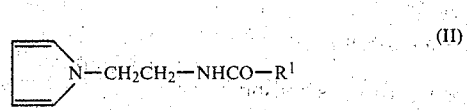

in which $R^1$ is as defined herein with an acid catalyst to obtain the corresponding compound of formula IV

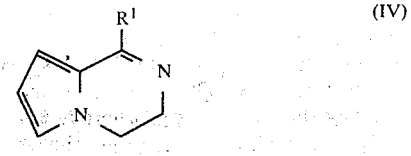

in which $R^1$ is as defined herein and reducing the compound of formula IV to obtain the corresponding compound of formula I in which $R^1$ is as defined herein and $R^2$ is hydrogen; or (b) reacting the compound of formula IV with a halide of formula $R^2$—X in which $R^2$ is lower alkyl, cyclo(lower)alkyl, 2-(indole-3-yl)ethyl or phenyl(lower)alkylene and X is bromo, chloro or iodo to obtain the corresponding compound of formula V

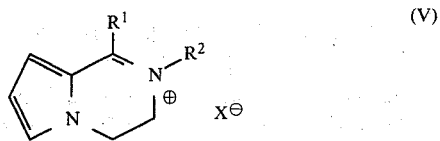

in which $R^1$ is as defined herein and $R^2$ is lower alkyl, cyclo(lower)alkyl, 2-(indole-3-yl)ethyl or phenyl(lower)alkylene and reducing the compound of formula V to obtain the corresponding compound of formula I in which $R^1$ is as defined herein and $R^2$ is lower alkyl, cyclo(lower)alkyl, 2-(indole-3-yl)ethyl or phenyl(lower)alkylene; or (c) condensing a compound of formula III

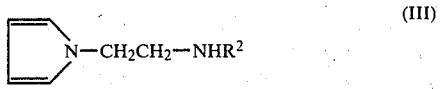

in which $R^2$ is hydrogen or a lower alkyl of formula —$CH_2$—$R^4$ wherein $R^4$ is a lower alkyl of one to five carbon atoms with an aldehyde of formula $R^1$—CHO in which $R^1$ is as defined herein to obtain the corresponding compound of formula I in which $R^1$ is as defined herein and $R^2$ is hydrogen or a lower alkyl of formula —$CH_2$—$R^4$ wherein $R^4$ is as defined herein; or (d) reacting the compound of formula I in which $R^1$ is as defined herein and $R^2$ is hydrogen with a halide of formula $R^2$—X in which $R^2$ is lower alkyl, cyclo(lower)alkyl, 2-(indole-3-yl)ethyl or phenyl(lower)alkylene and X is bromo, chloro or iodo to obtain the corresponding compound of formula I in which $R^1$ is as defined herein and $R^2$ is lower alkyl, cyclo(lower)alkyl, 2-(indole-3-yl)ethyl or phenyl(lower)alkylene; or (e) reacting the compound of formula I in which $R^1$ is as defined herein and $R^2$ is hydrogen with an acyl halide of formula $R^5$—CO—X in which $R^5$ is lower alkyl containing one to five carbon atoms or phenyl(lower)alkylene wherein the (lower)alkylene portion thereof contains one to five carbon atoms to obtain the corresponding intermediate of formula VI

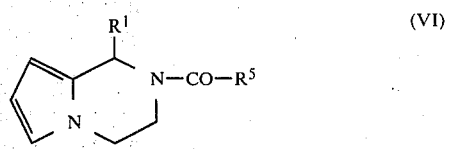

in which $R^1$ and $R^5$ are as defined herein and reducing the compound of formula VI to obtain the corresponding compound of formula I in which $R^1$ is as defined herein and $R^2$ is a radical of formula $—CH_2—R^5$ wherein $R^5$ is as defined herein; and when required, reacting the compound of formula I with a therapeutically acceptable acid to obtain the corresponding therapeutically acceptable addition salt of the compound of formula I in which $R^1$ and $R^2$ are as defined herein.

The compounds of formula I are useful for treating depression in a mammal. Accordingly, an effective antidepressant amount of a compound of formula I, or a therapeutically acceptable acid addition salt is administered to said mammal. The compound of formula I, or a therapeutically acceptable acid addition salt thereof, and a pharmaceutically acceptable carrier form a useful pharmaceutical composition for treating depression in the above manner.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, isopropyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexyloxy and the like.

The term "lower alkylene" as used herein means a divalent organic radical derived from either straight or branched chain aliphatic hydrocarbons containing from one to six carbon atoms by removal of two hydrogen atoms and includes methylene, ethylene, 1-methylpropylene, 2-ethylpropylene, 2-butylethylene and the like.

The term "cyclo(lower)alkyl" as used herein means saturated cyclic hydrocarbon radicals containing from three to six carbon atoms and includes cyclopropyl, cyclobutyl, cyclopentyl and cyclohexyl and the like.

The term "lower alkanol" as used herein means both straight and branched chain alkanols containing from one to four carbon atoms and includes methanol, ethanol, isopropanol, butanol and the like.

The term "organic proton acceptor" as used herein means the organic bases or amines for instance, triethylamine, pyridine, N-ethylmorpholine, 1,5-diazabicyclo[3.4.0]nonene-5 and the like.

The term "complex borohydride" as used herein means the metal borohydrides, including sodium borohydride, potassium borohydride, lithium borohydride, zinc borohydride and the like, and metal trihydrocarbyl-borohydrides including lithium 9-alkyl-9-borabicyclo[3,3,1]-nonylhydride, in which the alkyl contains one to seven carbon atoms, preferably lithium 9-tert-butyl-9-borabicyclo[3,3,1]nonylhydride, prepared according to the procedure described in German Offenlegungsschrift No. 2,207,987, published Aug. 31, 1972, lithium diisopinocamphenyl-tert-butylborohydride and lithium 2-thexyl-4,8-dimethyl-2-borobicyclo[3,3,1]nonylhydride, described by E. J. Corey et al., J. Amer. Chem. Soc., 93, 1491 (1971), lithium perhydro-9b-borophenalyhydride, described by H. C. Brown and W. C. Dickason, J. Amer. Chem. Soc., 92, 709(1970) and the like.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes, it is preferable to administer the salts rather than the base compound. Examples of suitable acids to form these salts include: the common mineral acids, e.g. hydrohalic, sulfuric or phosphoric acids; the organic acids, e.g., formic, acetic, maleic, malic, citric, or tartaric acid; and acids which are sparingly soluble in body fluids and which impart slow-release properties to their respective salts, e.g., pamoic acid tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I. Such stereochemical isomers are obtained in substantially pure form by classical separation techniques and by sterically controlled synthesis.

Individual optical enantiomers, which might be separated by fractional crystallization of the diastereomeric salts thereof, for instance salts with d- or l-tartaric acid or d-α-bromocamphor sulfonic acid, are also included.

The compounds of formula I are central nervous system agents exhibiting antidepressant activity of the type exhibited by amitriptyline, nortriptyline and imipramine. The antidepressant activity of the compounds of formula I, or their acid addition salts with therapeutically acceptable acids, is demonstrated in standard pharmacologic tests such as, for example, the test described by P. V. Petersen et al., Acta. Pharmacol. Toxicol., 24, 121 (1966).

More specifically, as noted in the above reference, the antidepressant properties of a compound can be demonstrated by its capacity to prevent the depressant effects of reserpine. Furthermore, it is well documented that reserpine in animals produces a model depression which can be used for detecting antidepressant properties. Accordingly, the compounds of formula I are shown to be effective antidepressant agents by a modification of the prevention of the reserpine-induced ptosis in mice, described by P. V. Petersen et al., cited above.

In this method, male albino mice weighing from 18–24 grams are used. A solution of 0.4 mg/ml of reserpine is prepared. This is administered subcutaneously to a group of ten mice at a volume of 0.2 ml/20 g (4 mg/kg). Immediately following this, the same animals are similarly injected with the test compound solution i.p.

A control is establishd by substituting saline solution for the test compound in the above procedure.

After 90 minutes, the mice are successively lifted from their cages by their tails, shaken and placed on the table. Their eyes are then inspected for ptosis. The number of animals with open eyes is noted. The observation is based on all or none response. The animals with open eyes are considered to be protected from reserpine-induced ptosis.

Using the above method, the compounds of the present invention prevent ptosis in mice at doses ranging from about 10 to 200 mg per kilogram of body weight. For example, the following compounds of formula I are effective antidepressant agents when administered intraperitoneally to the mouse (the effective i.p. dose to achieve the indicated percent protection in mg per kilogram of body weight is given in the parentheses): 1,2,3,4-tetrahydro-1-methylpyrrolo(1,2-a)pyrazine described in Example 3, dose of 56–65 mg gives 50% protection) and 2-ethyl-1,2,3,4-tetrahydro-1-phenylpyrrolo(1,2-a)pyrazine (described in Example 10, dose of 40 mg gives 30% protection).

When the compounds of formula I of this invention are used as antidepressant agents in mammals, e.g., rats and dogs, they are used alone or in combination with pharmacologically acceptable carriers, the proportion of which is determined by the solubility and chemical nature of the compound, chosen route of administration and standard biological practice. For example, they are administered orally in solid form, e.g., capsule or tablet. They can also be administered orally in the form of suspensions or solutions or they can be injected parenterally. For parenteral administration they are used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methyl-cellulose, sodium alginate, gum acacia, lecithin and so forth. The aqueous suspensions can also contain one or more preservatives, one or more coloring agents, one or more flavouring agents and one or more sweetening agents.

Non-aqueous suspensions can be formulated by suspending the active ingredient in a vegetable oil, for example, arachic oil, olive oil, sesame oil, or coconut oil, or in a mineral oil. The suspension can contain a thickening agent, for example beeswax, hard paraffin or cetyl alcohol. These compositions can also contain a sweetening agent, flavouring agent and antioxidant.

The dosage of the compounds of formula I of this invention as antidepressant agents will vary with the form of administration and the particular compound chosen. Furthermore, it will vary with the particular host, as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective antidepressant amount of the compounds usually ranges from about 1.0 mg to about 500 mg per kilogram of body weight per day, although as aforementioned variations will occur. However, a dosage level that is in the range of from about 10 mg to about 200 mg per kilogram of body weight per day is employed most desirably in order to achieve effective results.

PROCESS

For the preparation of the 1,2,3,4-tetrahydropyrrolo(1,2-a)pyrazine derivatives of formula I, the preferred starting materials are the compounds of formulae II and III. A preferred method of preparing these starting materials is illustrated in reaction scheme I.

REACTION SCHEME I

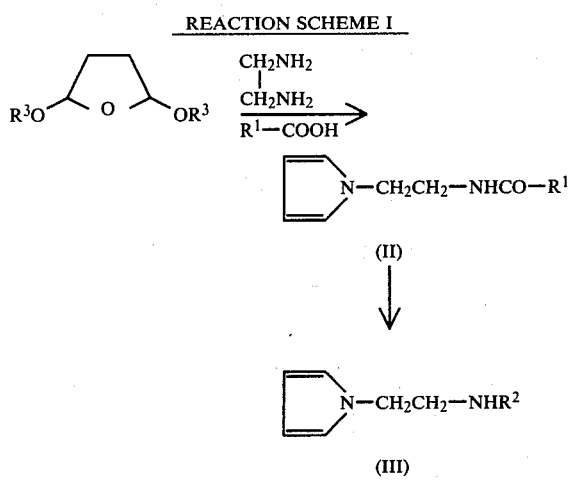

With reference to reaction scheme I, condensation of a 2,5-di(lower alkoxy)tetrahydrofuran, illustrated by the first formula in which $R^3$ is lower alkyl, ethylenediamine and a carboxylic acid of formula $R^1$-COOH in which $R^1$ is as defined herein gives the corresponding compound of formula II in which $R^1$ is as defined herein. With respect to the 2,5-di(lower alkoxy)tetrahydrofuran, 1.0 to 5.0 molar equivalents, preferably 1.1 to 1.4 molar equivalents of ethylenediamine, and 3.0 to 10.0 molar equivalents, preferably 3.0 to 6.0 molar equivalents, of the carboxylic acid of formula $R^1$-COOH usually are used. Preferred conditions include at least two molar equivalents of the carboxylic acid with respect to ethylenediamine plus at least one molar equivalent of the carboxylic acid with respect to 2,5-di(lower alkoxy)tetrahydrofuran. Suitable solvents for the reaction are selected from tetrahydrofuran, dioxane and lower alkanols, i.e. ethanol, propanol, isopropanol, butanol, hexanol or other $C_{2-6}$ alcohols, the preferred solvent being dioxane. The reaction mixture is maintained at 50° to 105° C. for one to ten hours, preferably at 70° to 100° C. for two to seven hours and the corresponding compound of formula II is isolated by extraction with a water immiscible organic solvent.

Alkaline hydrolysis of the compound of formula II with a 5 to 20% aqueous solution of two to ten molar equivalents of sodium or potassium hydroxide at 80° to 100° C. for one to ten hours gives the corresponding compound of formula III in which $R^2$ is hydrogen.

Alternatively, the compound of formula II in which $R^1$ is lower alkyl containing one to five carbon atoms can be reduced with three to six molar equivalents of lithium aluminum hydride at 20° to 60° C. for 3 to 30 hours in an anhydrous inert organic solvent, preferably diethyl ether or tetrahydrofuran, to obtain the corresponding compound of formula III in which $R^2$ is a lower alkyl of the formula —CH$_2$—R$^4$ wherein R$^4$ is a lower alkyl containing one to five carbon atoms.

If desired, the compound of formula III in which R$^2$ is hydrogen can be converted to a compound of formula II. For example, reaction of the compound of formula III in which R$^2$ is hydrogen with 1.1 to 2.0 molar equivalents of an acid halide of formula R$^1$—CO—X wherein R$^1$ is as defined herein and X is bromo or chloro in the presence of 1.1 to 2.0 molar equivalents of an organic proton acceptor, preferably triethylamine or N-ethylmorpholine, in an inert organic solvent, preferably tetrahydrofuran, dioxane, dimethylformamide, diethyl ether or ethyl acetate, at 0° to 50° C. for 10 to 50 hours gives the corresponding compound of formula II in which R$^1$ is as defined herein.

Conversion of the compound of formula II to the corresponding compound of formula I is illustrated in reaction scheme 2.

REACTION SCHEME 2

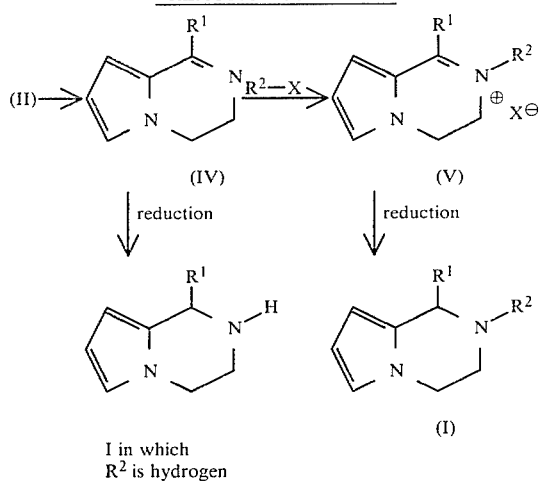

I in which
R$^2$ is hydrogen

With reference to reaction scheme 2, the compound of formula II is cyclized with an acid catalyst to obtain the corresponding 3,4-dihydropyrrolo(1,2-a)pyrazine of formula IV in which R$^1$ is as defined herein. Suitable acid catalysts are selected from the type used for a Friedel-Crafts reaction, for example, polyphosphoric acid, sulfuric acid, aluminum chloride, phosphorus pentoxide, phosphorus oxychloride, boron trifluoride, perchloric acid, trifluoroacetic acid, hydrogen chloride, p-toluenesulfonic acid or mixtures thereof. A preferred acid catalyst is selected from polyphosphoric acid, sulfuric acid, phosphorus oxychloride, hydrogen chloride or p-toluenesulfonic acid. The amount of acid catalyst can vary from 1.0 base equivalents of the acid to a large molar excess. A preferred amount of acid catalyst is in the range of 1.0 to 5.0 base equivalents of the acid. For example, if sulfuric acid is used, then a minimum of 0.5 molar equivalents of the acid can be used or if hydrogen chloride is used, then a minimum of 1.0 molar equivalents of the acid can be used. The cyclization can be performed using only a mixture of N-[2-(pyrrol-1-yl)ethyl]formamide and the acid catalyst without a solvent or the cyclization can be performed in an inert organic solvent.

Suitable inert organic solvents are selected from toluene, benzene and methanol. To achieve cyclization, the reaction mixture is heated at 0° to 120° C. for 10 minutes to 5 hours. The preferred temperature of the reaction is related to the acid catalyst used. For example, when polyphosphoric acid is used, the reaction mixture is heated at 70° to 100° C. for 10 minutes to 3 hours and when hydrogen chloride, phosphorus oxychloride or sulfuric acid are used, the reaction mixture is maintained at 0° to 30° C. for one to three hours.

Reduction of the compound of formula IV gives the corresponding compound of formula I in which R$^1$ is as defined herein and R$^2$ is hydrogen. A number of methods and reagents can be used for this reduction, for example, zinc in acetic acid, borane, a complex borohydride and hydrogen in the presence of a noble metal hydrogenation catalyst, for example, platinum or palladium on carbon. The preferred method of reduction uses three to five molar equivalents of sodium borohydride (a complex borohydride) in a lower alkanol, preferably methanol or ethanol, or a 1 to 15% aqueous solution of a lower alkanol. This solution is maintained at 20° to 30° C. for 10 to 30 hours and the compound of formula I in which R$^1$ is as defined herein and R$^2$ is hydrogen is isolated.

As illustrated in reaction scheme 2, the compound of formula IV can be converted to the compound of formula V which is reduced to obtain the corresponding compound of formula I in which R$^1$ and R$^2$ are as defined herein. In this conversion, the compound of formula IV is reacted with 1.0 to 1.5 molar equivalents of a halide of formula R$^2$—X in which R$^2$ is lower alkyl, cyclo(lower)alkyl, 2-(indole-3-yl)ethyl or phenyl(lower)alkylene and X is bromo, chloro or iodo at 75° to 220° C. for 10 minutes to 20 hours to obtain the corresponding compound of formula V in which R$^1$ is as defined herein and R$^2$ is as defined immediately above. For this reaction, a solvent is usually not used if the reactants are mutually soluble. However, if it is desirable to use a solvent, any inert organic solvent can be used, for example, a lower alkanol, preferably ethanol.

Reduction of the compound of formula V, in the same manner as described above for the reduction of the compound of formula IV, affords the corresponding compound of formula I in which R$^1$ is as defined herein and R$^2$ is as defined immediately above.

Another method is also useful for preparing some compounds of formula I. In this method, the compound of formula III in which R$^2$ is hydrogen or a lower alkyl of formula —CH$_2$—R$^4$ wherein R$^4$ is as defined herein is condensed with 1.0 to 1.5 molar equivalents of an aldehyde of formula R$^1$—CHO in which R$^1$ is as defined herein at 20° to 40° C. for 10 to 60 hours in an inert organic solvent, preferably acetic acid, to obtain the corresponding compound of formula I in which R$^1$ is hydrogen or a lower alkyl of formula —CH$_2$—R$^4$ wherein R$^4$ is as defined herein and R$^2$ is as defined herein.

In addition, the compound of formula I in which R$^1$ is as defined herein and R$^2$ is hydrogen can be reacted with a halide of formula R$^2$—X in which R$^2$ is lower alkyl, cyclo(lower)alkyl, 2-(indole-3-yl)ethyl or phenyl(lower)alkylene and X is bromo, chloro or iodo, in the same manner as described above for the reaction of the compound of formula IV with a halide of formula R$^2$—X, to obtain the corresponding compound of formula I in which R$^1$ is as defined herein and R$^2$ is lower alkyl, cyclo(lower)alkyl, 2-(indole-3-yl)ethyl or phenyl(lower)alkylene.

Still another method useful for preparing some compounds of formula I involves the following reactions of acylation and reduction. The compound of formula I in which $R^1$ is as defined herein and $R^2$ is hydrogen is acylated with an acyl halide of formula $R^5$—CO—X in which $R^5$ is lower alkyl containing one to five carbon atoms, or phenyl(lower)alkylene wherein the (lower)alkylene portion thereof contains one to five carbon atoms, in the same manner as described above for the acylation of the compound of formula III with an acyl halide of formula $R^1$—CO—X, to obtain the corresponding intermediate of formula VI in which $R^1$ and $R^5$ are as defined herein.

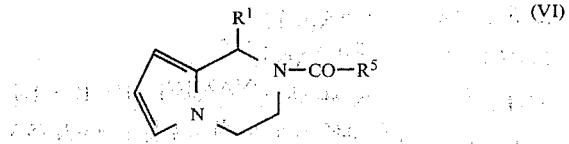

(VI)

Reduction of the compound of formula VI, preferably with lithium aluminum hydride in the same manner as described above for the reduction of the compound II in which $R^1$ is lower alkyl, gives the corresponding compound of formula I in which $R^1$ is as defined herein and $R^2$ is a radical of formula —$CH_2$—$R^5$ wherein $R^5$ is as defined herein.

The following examples illustrate further this invention.

EXAMPLE 1

N-[2-(1H-PYRROL-1-YL)ETHYL]ACETAMIDE (II; $R^1$=Me)

A mixture of ethylenediamine (12 g), 2,5-dimethoxytetrahydrofuran (29 g), dioxane (400 ml), and acetic acid (200 ml) is refluxed for 4 hr and then stirred at 20° to 30° C. for 10 hr. The solvents are removed under reduced pressure, the residue is dissolved in chloroform and the solution is washed successively with conc. sodium bicarbonate and water. The organic phase is dried over magnesium sulfate, filtered and evaporated. The residue is crystallized from ethyl acetate-diethyl ether to give the title compound (20 g): mp 59°–60° C., ir($CHCl_3$) 3420 and 1660 $cm^{-1}$, nmr-($CDCl_3$) δ 1.92(s), 3.25(dd), 3.62(dd), 3.99(dd), 4.06(dd), 6.00(s), 6.18(t) and 6.77(t), and anal. calc'd. for $C_8H_{12}N_2O$: C, 63.13% H, 7.95% N, 18.41% and found: C, 63.27% H, 7.87% N, 18.51%.

In the same manner but replacing acetic acid with an equivalent amount of 2-methylpropanoic acid, the following compound of formula II is obtained, N-[2-(1H-pyrrol-1-yl)ethyl]-2-methylpropanamide: ir($CHCl_3$) 3440 and 1650 $cm^{-1}$ and nmr($CDCl_3$) δ 1.2(d), 2.28(m), 3.47(m), 3.98(m), 5.45(s), 6.14(m) and 6.62(m).

Similarly, by replacing acetic acid with an equivalent amount of butanoic acid or 3,3-dimethylbutanoic acid, the following compounds of formula II are obtained, respectively:
N-[2-(1H-pyrrol-1-yl)ethyl]butanamide and
N-[2-(1H-pyrrol-1-yl)ethyl]-3,3-dimethylbutanamide.

EXAMPLE 2

3,4-DIHYDRO-1-METHYLPYRROLO(1,2-a)PYRAZINE (IV; $R^1$=Me)

The solid N-[2-(1H-pyrrol-1-yl)ethyl]acetamide (8 g, described in Example 1) is added cautiously in small portions into phosphorus oxychloride (45 ml) upon stirring. The mixture is refluxed for 60 min and evaporated under reduced pressure (1 mm Hg). The residue is partitioned between 10% sodium hydroxide and diethyl ether, and the organic phase is separated and evaporated. The residue is filtered through a column of neutral alumina packed in chloroform and the eluates are evaporated to obtain 6.7 g of the title compound which solidified: mp 25°–27° C. and nmr($CDCl_3$) δ 2.28(s), 3.84(s), 6.12(t), 6.36(d) and 6.64.

In the same manner but replacing N-[2-(1H-pyrrol-1-yl)ethyl]acetamide with an equivalent amount of another compound of formula II described in Example 1, the following compounds of formula IV are obtained, respectively:
3,4-dihydro-1-(1-methylethyl)pyrrolo(1,2-a)pyrazine,
3,4-dihydro-1-propylpyrrolo(1,2-a)pyrazine and
3,4-dihydro-1-(2,2-dimethylpropyl)pyrrolo(1,2-a)pyrazine.

EXAMPLE 3

1,2,3,4-TETRAHYDRO-1-METHYLPYRROLO(1,2-a)PYRAZINE (I; $R^1$=Me and $R^2$=H)

The solid N-[2-(1H-pyrrol-1-yl)ethyl]acetamide (8 g, described in Example 1) is added cautiously in small portions into phosphorus oxychloride (45 ml) upon stirring. The mixture is refluxed for 60 min, and evaporated under reduced pressure (1 mm Hg). The residue is dissolved in 600 ml of methanol, filtered, and diluted with 60 ml of water. Sodium borohydride (8 g) is then added over 40 min at 25° C. The reaction mixture is stirred overnight, concentrated in vacuo, rendered basic with 10% ammonium hydroxide, and extracted with chloroform. The extracts are dried and evaporated to give a residue (5.79) of the title compound, nmr($CDCl_3$) δ 1.38(d), 1.90(s), 3.25(m), 3.80(d), 3.86(d), 4.05(q), 5.85(dd), 6.14(t) and 6.53(dd). A solution of the title compound in ethanol and a solution of an equimolar amount of maleic acid in ethanol are combined. The resulting solution is concentrated to obtain the maleate salt of the title compound: mp 137°–138° C., uv(MeOH) λmax 210 nm; ε=15000, and anal. calc'd. for $C_8H_{12}N_2 \cdot C_4H_4O_4$: C, 57.13% H, 6.39% N, 11.11% and found: C, 57.16% H, 6.44% N, 10.86%.

In the same manner but replacing N-[2-(1H-pyrrol-1-yl)ethyl]acetamide with an equivalent amount of another compound of formula II described in Example 1, the following compounds of formula I are obtained, respectively:
1,2,3,4-tetrahydro-1-(1-methylethyl)pyrrolo(1,2-a)pyrazine,
1,2,3,4-tetrahydro-1-propylpyrrolo(1,2-a)pyrazine and
1,2,3,4-tetrahydro-1-(2,2-dimethylpropyl)pyrrolo(1,2-a)pyrazine.

EXAMPLE 4

1,2,3,4-TETRAHYDRO-1,2-DIMETHYLPYRROLO(1,2-a)PYRAZINE (I; $R^1$ and $R^2$=Me)

A solution of 3,4-dihydro-1-methylpyrrolo(1,2-a)pyrazine (4.5 g, described in Example 2) and methyl iodide (9 ml) in ethanol (60 ml) is refluxed for 15 hr and evaporated. The residue is crystallized from methanol-diethyl ether to obtain 3,4-dihydro-1,2-dimethylpyrrolo(1,2-a)pyrazinium iodide (6.0 g), mp 166°–168° C.

A solution of the latter compound (5.5 g) in methanol (200 ml) and water (5 ml) is treated with sodium borohydride (6 g in small portions) over a period of 2 hr. The reaction mixture is stirred overnight at room temperature and evaporated. The residue is partitioned between chloroform and water. The organic phase is concentrated and chromatographed on silica gel. Elution with chloroform-methanol 20:1 afforded a homogeneous fraction (1.7 g) of the title compound, nmr(CDCl$_3$) δ 1.42(d), 2.55–3.50(m), 3.65–4.30(m), 5.84(m), 6.12(m) and 6.47(m).

Equimolar amounts of the title compound and maleic acid are dissolved in ethanol. Diethyl ether is added and the precipitate is collected and crystallized from maleate salt of the title compound: mp 136°–137° C. uv(MeOH) λmax 210 nm; ε=24210 and anal. calc'd. for C$_9$H$_{14}$N$_2$·C$_4$H$_4$O$_4$: C, 58.63% H, 6.81% N, 10.52% and found: C, 58.60% H, 6.69% N, 10.37%.

In the same manner but replacing 3,4-dihydro-1-methylpyrrolo(1,2-a)pyrazine with another compound of formula IV described in Example 2, the following compound of formula I are obtained, respectively:

1,2,3,4-tetrahydro-2-methyl-1-(2-methylethyl)pyrrolo(1,2-a)pyrazine, 1,2,3,4-tetrahydro-2-methyl-1-propylpyrrolo(1,2-a)pyrazine, and 1,2,3,4-tetrahydro-2-methyl-1-(2,2-dimethylpropyl)pyrrolo(1,2-a)pyrazine.

EXAMPLE 5

1,2,3,4-TETRAHYDRO-1-METHYL-2-(2-PHENYLETHYL)PYRROLO(1,2-a)PYRAZINE (I; R$^1$=Me AND R$^2$=2-PHENYLETHYL)

A mixture of 3,4-dihydro-1-methylpyrrolo(1,2-a)pyrazine (3.4 g, described in Example 2) and phenylethyl bromide (5 g) is heated at reflux for 50 min. The resultant solid is dissolved in 150 ml of methanol and 20 ml of water, and 4 g of sodium borohydride is added in small portions over 1 hr. Stirring is continued for 15 hr at room temperature and the solvents are evaporated. The residue is partitioned between 5% sodium hydroxide and chloroform. The organic phase is washed with water, concentrated and chromatographed on a column of silica gel using chloroform. The eluates are evaporated to give the title compound (3.0 g), nmr(CDCl$_3$) δ 1.37(d), 2.5–3.5(m), 3.80(q), 3.98(m), 5.89(m), 6.18(t), 6.53(dd) and 7.25(m).

The maleate salt of the title compound is prepared in the same manner as described in Example 4 and crystallized from ethanol-diethyl ether: mp 132°–133° C. and anal. calc'd. for C$_{16}$H$_{20}$N$_2$·C$_4$H$_4$O$_4$: C, 67.39% H, 6.79% N, 7.86% and found: C, 67.42% H, 6.78% N, 7.71%.

In the same manner but replacing phenylethyl bromide with an equivalent amount of cyclobutyl bromide, cyclohexyl iodide, 3-methylbutyl bromide or 2-ethyl-3-phenylpropyl bromide, the following compounds of formula I are obtained, respectively:

2-cyclobutyl-1,2,3,4-tetrahydro-1-methylpyrrolo(1,2-a)pyrazine, 2-cyclohexyl-1,2,3,4-tetrahydro-1-methylpyrrolo(1,2-a)pyrazine, 1,2,3,4-tetrahydro-1-methyl-2-(3-methylbutyl)pyrrolo(1,2-a)pyrazine and 2-(2-ethyl-3-phenylpropyl)-1,2,3,4-tetrahydro-1-methylpyrrolo-(1,2-a)pyrazine.

EXAMPLE 6

1-METHYL-2-[2-(INDOLE-3-YL)ETHYL]-1,2,3,4-TETRAHYDRO-PYRROLO(1,2-a)PYRAZINE I; R$^1$=Me and R$^2$=2-(INDOLE-3-YL)ETHYL)

A mixture of 3,4-dihydro-1-methylpyrrolo(1,2-a)pyrazine (3.47 g, described in Example 2) and 2-(indole-3-yl)ethyl bromide (5.8 g) is dissolved in 10 ml of water and 200 ml of methanol. Sodium borohydride (3.5 g) is added in small portions over 20 min, and the mixture was stirred at room temperature for 24 hr. The solvents are evaporated and the residue is partitioned between chloroform and 5% sodium hydroxide. The organic phase is washed with water, concentrated and chromatographed through a column of silica gel using chloroform. The eluates are evaporated to give the title compound (2.4 g), nmr(CDCl$_3$) δ 1.44(d), 2.56–3.52(m), 3.67–4.17(m), 5.94(m), 6.21(t), 6.58(dd), 7.00(d), 7.22(m), 7.68(m) and 8.12(s).

EXAMPLE 7

2-(1H-PYRROL-1-YL)ETHANAMINE (III; R$^2$=H)

A mixture of N-[2-(1H-pyrrol-yl)ethyl]acetamide (5.3 g, described in Example 1) in 10% aqueous potassium hydroxide (100 ml) is refluxed for 2 hr. After cooling, the mixture is extracted with chloroform and the organic extracts are washed with 100 ml of 10% hydrochloric acid. This aqueous solution is separated and rendered basic with 50% aqueous sodium hydroxide. The aqueous alkaline solution is extracted with chloroform. The organic extract is dried and evaporated to give the title compound as an oil, bp 50°–51° C./2mm Hg.

EXAMPLE 8

1,2,3,4-TETRAHYDRO-1-(3,4,5-TRIMETHOXYPHENYL)PYRROLO(1,2-a)PYRAZINE (I; R$^1$=3,4,5-trimethoxyphenyl and R$^2$=H)

A solution of 3,4,5-trimethoxybenzaldehyde (19.6 g) and 2-(1H-pyrrol-1-yl)ethanamine (11 g, described in Example 7) in acetic acid (250 ml) is stirred at room temperature for 48 hr and evaporated under reduced pressure. The residue is partitioned between chloroform and 10% sodium carbonate and the organic phase is separated, washed with water, dried over magnesium sulfate, filtered and evaporated to give 18 g of the title compound, nmr(CDCl$_3$) δ (2.40(s), 3.35(m), 3.84(s), 3.92(m), 5.03(s), 5.65(m), 6.12(t), 6.61(m) and 6.70(s).

The maleate salt of the title compound is prepared in the same manner as described in Example 4 and crystallized from acetonitrilediethyl ether: mp 178°–179° C. and anal. calc'd. for C$_{16}$H$_{20}$N$_2$O$_3$·C$_4$H$_4$O$_4$: C, 59.40% H, 5.98% N, 6.93% and found: C, 59.00% H, 5.94% N, 7.19%.

In the same manner but replacing 3,4,5-trimethoxybenzaldehyde with an equivalent amount of 3-methylbenzaldehyde, 4,5-diethylbenzaldehyde, 4-propoxybenzaldehyde, cyclopentylcarboxaldehyde or pentanal, the following compounds of formula I are obtained, respectively:

1,2,3,4-tetrahydro-1-(3-methylphenyl)pyrrolo(1,2-a)pyrazine, 1,2,3,4-tetrahydro-1-(4,5-diethylphenyl)pyrrolo(1,2-a)pyrazine, 1,2,3,4-tetrahydro-1-(4-propoxyphenyl)pyrrolo(1,2-a)pyrazine, 1-cyclopentyl-1,2,3,4-tetrahydropyrrolo(1,2-a)pyrazine and 1-butyl-1,2,3,4-tetrahydropyrrolo(1,2-a)pyrazine.

EXAMPLE 9

N-ETHYL-2-(1H-PYRROL-1-YL)ETHANAMINE (III; R² = Et)

To a stirred suspension of lithium aluminum hydride (10 g) in dry diethyl ether (500 ml) is added dropwise a solution of N-[2-(1H-pyrrol-1-yl)ethyl]acetamide (10 g, described in Example 1) in dry tetrahydrofuran (250 ml). The mixture is refluxed for 3 hr, stirred overnight at room temperature, and decomposed with 10 ml of water, 10 ml of 15% sodium hydroxide, and 30 ml of water. The resultant slurry is stirred for 90 min and filtered. The filtrate is dried over magnesium chloride and evaporated to give the title compound as an oil: bp 70° C./8 mm Hg and nmr(CDCl₃) δ 1.06(t), 1.64(s), 2.65(q), 2.95(t), 4.03(t), 6.19(t) and 6.70(t).

In the same manner but replacing N-[2-(1H-pyrrol-1-yl)ethyl]acetamide with an equivalent amount of another compound of formula II described in Example 1, the following compounds of formula III are obtained respectively:
N-(2-methylpropyl)-2-(1H-pyrrol-1-yl)ethamine,
N-butyl-2-(1H-pyrrol-1-yl)ethanamine and
N-(3,3-dimethylbutyl)-2-(1H-pyrrol-1-yl)ethanamine.

EXAMPLE 10

2-ETHYL-1,2,3,4-TETRAHYDRO-1-PHENYLPYRROLO(1,2-a)PYRAZINE (I; R¹=Ph and R²=Et)

A solution of benzaldehyde (7.4 g) and N-ethyl-2-(1H-pyrrol-1-yl)ethanamine (9.5 g, described in Example 9) in acetic acid (90 ml) is stirred at room temperature for 24 hr and evaporated. The residue is partitioned between chloroform and 5% sodium hydroxide. The organic phase is separated, washed with water, dried over magnesium sulfate, filtered and evaporated. The residue is chromatographed on a column of silica using chloroform. The eluates are evaporated to give the title compound (7.8 g), nmr(CDCl₃) δ 1.01(t), 1.93-3.0(m), 3.19(d), 3.41(d), 4.17(m), 4.50(s), 5.39(m), 6.10(t), 6.57(t) and 7.33(m).

The maleate salt of the title compound is prepared in the same manner as described in Example 4 and crystallized from ethanol-diethyl ether: mp 103°-104° C. and anal. calc'd. for $C_{15}H_{18}N_2 \cdot C_4H_4O_4$: C, 66.65% H, 6.48% H, 8.18% and found: C, 66.63% H, 6.51% N, 8.17%.

In the same manner but replacing benzaldehyde with an equivalent amount of 3,4,5-trimethoxybenzaldehyde, 2-ethyl-1,2,3,4-tetrahydro-1-(3,4,5-trimethoxyphenyl)-pyrrolo(1,2-a)pyrazine, mp 118°-119° C. when crystallized from diethyl ether, and the corresponding hydrochloride salt, mp 173°-175° C. when crystallized from ethanol-diethyl ether, are obtained.

Similarly, by replacing N-ethyl-2-(1H-pyrrol-1-yl)ethanamine with an equivalent amount of another compound of formula III described in Example 9, the following compounds of formula I are obtained, respectively:
1,2,3,4-tetrahydro-2-(2-methylpropyl)-1-phenylpyrrolo(1,2-a)pyrazine,
2-butyl-1,2,3,4-tetrahydro-1-phenylpyrrolo(1,2-a)pyrazine and
1,2,3,4-tetrahydro-2-(3,3-dimethylbutyl)-1-phenylpyrrolo(1,2-a)pyrazine.

We claim:

1. A compound of formula I

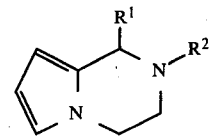

in which R¹ is lower alkyl, cyclo(lower)alkyl, phenyl or phenyl mono-, di- or trisubstituted with lower alkyl or lower alkoxy and R² is hydrogen, lower alkyl, cyclo(lower)alkyl, 2-(indole-3-yl)ethyl or phenyl(lower) alkylene or a therapeutically acceptable acid addition salt thereof.

2. The compound of claim 1 in which R¹ is lower alkyl, phenyl or phenyl mono-, di- or trisubstituted with lower alkyl or lower alkoxy and R² is hydrogen, lower alkyl, 2-(indole-3-yl)ethyl or phenyl(lower)alkylene.

3. The compound of claim 1 in which R¹ is lower alkyl, phenyl or 2,3,4-trimethoxyphenyl and R² is hydrogen, lower alkyl, 2-(indole-3-yl)ethyl or 2-phenylethyl.

4. 1,2,3,4-Tetrahydro-1-methylpyrrolo(1,2-a)pyrazine, as claimed in claim 1.

5. 1,2,3,4-Tetrahydro-1,2-dimethylpyrrolo(1,2-a)pyrazine, as claimed in claim 1.

6. 1,2,3,4-Tetrahydro-1-methyl-2-(2-phenylethyl)pyrrolo(1,2-a)pyrazine, as claimed in claim 1.

7. 1-Methyl-2-[2-(indol-3-yl)ethyl]-1,2,3,4-tetrahydropyrrolo(1,2-a)pyrazine, as claimed in claim 1.

8. 1,2,3,4-Tetrahydro-1-(3,4,5-trimethoxyphenyl)pyrrolo(1,2-a)pyrazine, as claimed in claim 1.

9. 2-Ethyl-1,2,3,4-tetrahydro-1-phenylpyrrolo(1,2-a)pyrazine, as claimed in claim 1.

10. 2-Ethyl-1,2,3,4-tetrahydro-1-(3,4,5-trimethoxyphenyl)pyrrolo(1,2-a)pyrazine, as claimed in claim 1.

11. A method of treating depression in a mammal, which comprises administering to said mammal an effective antidepressant amount of a compound of claim 1.

12. An antidepressant pharmaceutical composition, which comprises a compound of claim 1 and a pharmaceutically acceptable carrier in dosage unit form.